United States Patent [19]

Bohn

[11] Patent Number: 4,507,229

[45] Date of Patent: Mar. 26, 1985

[54] TISSUE PROTEIN PP$_4$, A PROCESS FOR ISOLATING IT AND ITS USE

[75] Inventor: Hans Bohn, Marburg, Fed. Rep. of Germany

[73] Assignee: Behringwerke Aktiengesellschaft, Marburg/Lahn, Fed. Rep. of Germany

[21] Appl. No.: 603,346

[22] Filed: Apr. 24, 1984

[30] Foreign Application Priority Data

Apr. 26, 1983 [DE] Fed. Rep. of Germany ....... 3315000

[51] Int. Cl.$^3$ ..................... C07G 7/00; A61K 35/42; A61K 35/50; A61K 39/395
[52] U.S. Cl. .......................... 260/112 B; 260/112 R; 260/112.5 R; 424/85; 424/88; 424/101; 514/2; 424/95; 424/99; 204/180 R
[58] Field of Search ................. 260/112 R, 112.5 R, 260/112 B; 424/95, 99, 101, 177, 85, 88

[56] References Cited

U.S. PATENT DOCUMENTS

| | | | |
|---|---|---|---|
| 4,041,021 | 8/1977 | Bohn | 260/112 B |
| 4,254,021 | 3/1981 | Bohn et al. | 260/112 B |
| 4,269,825 | 5/1981 | Bohn et al. | 424/85 |
| 4,297,343 | 10/1981 | Bohn et al. | 424/85 |
| 4,301,064 | 11/1981 | Bohn | 260/112 R |
| 4,302,385 | 11/1981 | Bohn et al. | 260/112 B |
| 4,325,866 | 4/1982 | Bohn | 260/112 B |
| 4,468,345 | 8/1984 | Bohn et al. | 260/112 R |

OTHER PUBLICATIONS

Placental and Pregnancy Proteins in Carcino-Embryonic Proteins, vol. I, Bohn, 1979, pp. 290-299.

*Primary Examiner*—Howard E. Schain
*Attorney, Agent, or Firm*—Finnegan, Henderson, Farabow, Garrett & Dunner

[57] ABSTRACT

The protein PP$_4$ which has
(a) an electrophoretic mobility in the range between that of $\alpha_1$ and $\alpha_2$ globulins;
(b) an isoelectric point of 4.85±0.15;
(c) a sedimentation coefficient $s_{20,w}^0$ of 3.3±0.2S;
(d) a molecular weight determined in polyacrylamide gel containing sodium dodecylsulfate (DSD) of 35,000±5,000;
(e) an extinction coefficient $E_1\,_{cm}^{1\%}$ (280 nm) of 5.9±0.6;
(f) a carbohydrate content of 2.4±0.94% (g/100 g) (mannose 0.3±0.2%, galactose 0.4±0.2%, xylose 0.1±0.4%, glucose 0.2±0.1%, glucosamine 1.0±0.2% and neuraminic acid 0.4±0.2%) and
(g) a specified aminoacid composition, and a process for its preparation are described. PP$_4$ can be used to prepare antisera which can be employed to detect and determine PP$_4$ in body fluids in order to diagnose diseases of particular organs, as a "marker" to monitor the progress of a disease or to check therapy.

4 Claims, 2 Drawing Figures

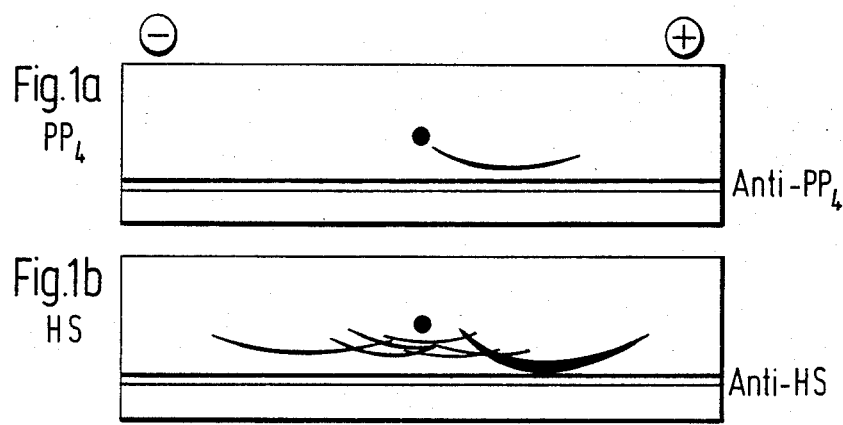

TISSUE PROTEIN PP4, A PROCESS FOR ISOLATING IT AND ITS USE

The invention relates to a tissue protein, which is called PP4, and to a process for isolating it.

PP4 can be used to prepare antisera which can be employed to detect and determine PP4 in body fluids in order to diagnose disorders of particular organs, and as a "marker" for monitoring the course of an illness or for checking therapy.

The invention relates to the protein PP4 which has the following characteristics:

(a) an electrophoretic mobility in the range between that of $\alpha_1$ and $\alpha_2$ globulins;
(b) an isoelectric point of $4.85 \pm 0.15$;
(c) a sedimentation coefficient $s_{20,w}^0$ of $3.3 \pm 0.2 S$;
(d) a molecular weight determined in polyacrylamide gel containing sodium dodecylsulfate (DSD) of $35,000 \pm 5,000$;
(e) an extinction coefficient $E_{1cm}^{1\%}$ (280 nm) of $5.9 \pm 0.6$;
(f) a carbohydrate content of $2.4 \pm 0.94\%$ (g/100 g) (mannose $0.3 \pm 0.2\%$, galactose $0.4 \pm 0.2\%$, xylose $0.1 \pm 0.04\%$, glucose $0.2 \pm 0.1\%$, glucosamine $1.0 \pm 0.2\%$ and neuraminic acid $0.4 \pm 0.2\%$) and
(g) the following aminoacid composition:

| Aminoacid | Residues per 100 residues (mol-%) | Coefficient of variation |
|---|---|---|
| lysine | 6.95 | 1.14 |
| histidine | 0.97 | 17.4 |
| arginine | 5.44 | 1.77 |
| aspartic acid | 11.41 | 1.68 |
| threonine | 6.78 | 2.40 |
| serine | 6.21 | 2.26 |
| glutamic acid | 12.25 | 0.43 |
| proline | 1.96 | 6.20 |
| glycine | 6.68 | 3.83 |
| alanine | 7.92 | 1.67 |
| cystine ½ | 0.77 | 19.5 |
| valine | 5.34 | 3.80 |
| methionine | 1.98 | 6.00 |
| isoleucine | 5.21 | 2.23 |
| leucine | 11.50 | 0.45 |
| tyrosine | 3.55 | 4.21 |
| phenylalanine | 4.07 | 3.77 |
| tryptophan | 0.93 | 23.9 |

The following details may be given to explain the identifying characteristics of the tissue protein:

The electrophoretic mobility was determined in the micro modification using a Microzone R 200 apparatus from Beckman Instruments on cellulose acetate films (supplied by Sartorius) and using sodium diethylbarbiturate buffer, pH 8.6.

The isoelectric point was determined using a column (440 ml) supplied by LKB, Stockholm. The Ampholin ® mixture had a pH range from 4.0 to 6.0.

The sedimentation coefficient was determined in an analytical ultracentrifuge supplied by Beckman (Spinco Apparatus, Model E) at 60,000 rpm in double-sector cells using the UV scanner technique at 280 nm. The solvent used was a 0.05 mol/l phosphate buffer (pH 6.8) which contained 0.2 mol/l NaCl. The protein concentration was adjusted to an optical density of about 3. The sedimentation coefficient was converted to the basis of water at 20° C.

To determine the molecular weights in polyacrylamide gel containing SDS, a gel containing 7.5 g of polyacrylamide (PAA) per 100 ml and 0.1 g of sodium dodecylsulfate (SDS) per 100 ml was used. The comparison substances used were human placental lactogen (HPL) and human albumin and its aggregates.

To determine the extinction coefficient, 1 mg of substance was dissolved in distilled water to give 1 ml of solution.

The carbohydrates were determined as follows: after hydrolysis of the glycosidic bonds, the liberated neutral sugars were separated as borate complexes on a column of anion exchanger (Y. C. Lee et al., Anal. Biochem. 27 (1969), 567), subjected in the eluate to a color reaction by admixture of Cu(I) bicinchoniate reagent (K. Mopper and M. Gindler, Anal. Biochem. 56 (1973), 440), and determined quantitatively using rhamnose as the internal standard. The aminosugars were detected and determined by their reaction with ninhydrin. The content of neuraminic acid was found by the method of Warren (Methods in Enzymology, Vol, VI (1963), 463–465).

The aminoacid analysis was carried out by the method of S. Moore, D. H. Spackman, W. H. Stein, Anal. Chem. 30 (1958), 1185, using a Multichrom B liquid chromatograph supplied by Beckman. Cystine was determined as cysteic acid after oxidation of the proteins with performic acid (S. Moore et al., Anal. Chem. 30 (1958), 1185) followed by chromatography (S. Moore, J. Biol. Chem. 238 (1963), 235). The tryptophan content was determined by direct photometry by the method of H. Edelhoch, Biochemistry 6 (1967), 1948.

On investigation of extracts from various human organs, PP4 was detected, using immunochemical methods, in relatively large concentrations in placenta, stomach, bladder, kidney, adrenals, skin and spleen. Extracts of other human organs, such as heart, lung, liver, colon, rectum and uterus, either did not contain this protein or contained it in considerably smaller amounts. PP4 occurs in low concentrations in the lysate of human erythrocytes (about 0.6 mg of PP4 per 100 ml of compact, washed erythrocytes). Proteins which are immunochemically identical or essentially related to PP4 have also been detected in extracts of placenta from monkeys and from cows and sheep.

Accordingly, organs and cells from humans or from animals, in which this protein appears, can be used to isolate PP4. Mature human placentae, which are produced in large amounts and contain the protein in a sufficiently high concentration, are particularly suitable for this purpose.

On average, a mature human placenta contains about 50 mg of PP4. The PP4 contained in the placenta is only partially dissolved (about 2 to 5 mg per placenta) on extracting the organ with dilute salt or buffer solutions, for example with physiological saline. However, the major part of the protein appears to be associated with membranes in the tissue and does not dissolve until solubilizing agents, for example non-ionic detergents, such as polyethylene glycol p-isooctylphenyl ether (Triton ® X-100) are used. Accordingly, both the protein extract from placentae isolated with dilute salt solutions and the protein extract of placentae obtained after washing the soluble constituents out of the tissue residue by solubilization with Triton ® X-100 can be used to obtain PP4. The proteins obtained by the two methods of extraction are identical in their physicochemical and immunochemical properties.

PP4 has the following properties which can be utilized in a process for its isolation by taking measures appropriate for these properties:

(1) It is precipitated from aqueous solution using ammonium sulfate at pH 7.0 and 40–75% saturation;
(2) It is precipitated with water-soluble acridine bases, for example 2-ethoxy-6,9-diaminoacridine lactate (Rivanol ®) at pH values between 4 and 9 and at a concentration of base of 0.2 to 0.8 g/100 ml. It is partially precipitated at a pH of 6.0 and a concentration of Rivanol of 0.4 g/100 ml.
(3) On electrophoretic separation, it is found in the region between $\alpha_1$ and $\alpha_2$ globulins at pH 8.6;
(4) On isoelectric focusing, it appears in the pH range from 4.7 to 5.0;
(5) On gel filtration with Sephadex ®, it behaves like proteins having molecular weights from 20,000 to 50,000;
(6) In dilute salt solutions at a conductivity of about 0–2 mS, it is adsorbed onto kaolin, for example bolus alba, supplied by Merck, Darmstadt, and can be eluted again from this using more concentrated salt solutions, for example 0.1 mol/l phosphate buffer, pH 6.8;
(7) It can be bound to weakly basic ion exchangers, for example DEAE cellulose or DEAE sephadex, at a conductivity of about 0–2 mS and a pH of about 7 to 9, and can be eluted with more concentrated salt solutions (1–5 g/100 ml salines);
(8) It can be concentrated and isolated from an aqueous solution by immunoadsorption.

Accordingly, the invention also relates to a process for isolating or concentrating PP4, which comprises subjecting an extract isolated with dilute salt or buffer solutions from organs which contain this protein to one or more of the following measures:

(a) precipitating the protein PP4 with ammonium sulfate in the pH range from 5 to 8 and at 40–70% saturation;
(b) precipitating the protein PP4 with a water-soluble acridine base at a pH between 4 and 9 and at a concentration of the base of 0.2–0.8 g/100 ml;
(c) preparative zone electrophoresis which entails the protein fraction between $\alpha_1$ and $\alpha_2$ globulins being isolated;
(d) gel filtration or ultrafiltration which entails proteins in the molecular weight range of 20,000 to 50,000 being isolated;
(e) adsorption on kaolin (Bolus alba, supplied by Merck, Darmstadt) and elution of the protein PP4;
(f) adsorption on a weakly basic ion exchanger and elution of the protein PP4;
(g) concentration by immunoadsorption.

For the precipitation of PP4, apart from ammonium sulfate it is also possible to use other neutral salts customarily employed in preparative biochemistry. Apart from an acridine base, a water-soluble derivative of a quinoline base, such as is known for protein fractionation, can also be employed within the framework of the process according to the invention. Moreover, for the isolation of the protein, it is also possible to use other measures which are appropriate for its electrophoretic behavior, its charge and its molecular weight, and which are suitable for separating a protein having the properties indicated from other proteins.

It is possible to use for this purpose the various methods of preparative electrophoresis, isoelectric focusing, gel filtration or ultrafiltration, or the property of PP4 of being able to be bound to weakly basic ion exchangers and eluted again from them.

However, in particular, the specific property of PP4 of being able to be adsorbed from dilute buffer solutions onto kaolin and to be eluted again from this using strong buffer solutions is excellently suitable for isolating this protein.

PP4 can be isolated by appropriate combination of the measures mentioned which bring about concentration of PP4 or separation of this protein from other proteins.

Thus, the invention also relates to a process for isolating or concentrating PP4, which comprises comminuting organs which contain this protein and washing them with physiological saline until all soluble constituents have been removed, extracting the tissue residue with a solution of a solubilizing agent, for example a non-ionic detergent, such as polyethylene glycol p-isooctylphenyl ether, and, after thorough dialysis, subjecting the resulting extract to one or more of the measures (a) to (g) described above.

In place of the non-ionic detergent, it is possible also to use, for example, a 3 mol/l KSCN solution or a 6 mol/l urea solution for solubilizing PP4.

The measures indicated for concentrating and isolating PP4 are by no means all obligatory, nor need they be carried out in the sequence indicated.

On isolating PP4 from the dilute salt extract of human placentae, it has proved to be advantageous first to fractionate the proteins in the extract using a water-soluble acridine base and ammonium sulfate, and then to concentrate them further by gel filtration before adsorbing them on kaolin (cf. Example 1).

On isolating PP4 from the protein fraction obtained by extraction of the placental tissue with detergent, it has proved to be advantageous first to concentrate PP4 by an immunoadsorption step and to follow this by gel filtration for further purification (cf. Example 2).

To detect and determine PP4, for example in a fraction from a separating operation, in addition to the indicated parameters it is also possible to use immunochemical methods, since PP4 has antigenic properties.

An antiserum which can be used for this purpose can be obtained in the following manner: a polyvalent antiserum, which contains, inter alia, antibodies against PP4, is obtained by immunizing rabbits with the protein fraction solubilized from placental tissue using detergent.

This antiserum can be used on the one hand for the immunological detection of PP4, and on the other hand for the preparation of an immunoadsorbent which can be used for concentrating and isolating PP4.

Monospecific antisera can be prepared by immunizing animals by known methods using the purified PP4 obtained in accordance with Example 1 of the present application.

FIG. 1a shows the immunological reaction of PP4 with a specific antiserum from rabbits after separation in an electric field in a gel containing agar.

By comparison,

FIG. 1b shows the separation of the proteins in the serum, which have been visualized by their immune reaction with a rabbit antiserum to human serum (HS).

For the immunological detection of PP4, it is also possible to use the Ouchterlony gel diffusion technique (cf. Schultze and Heremans, Molecular Biology of Human Proteins, Vol. 1, page 134) or, if necessary, more sensitive methods, such as radioimmunoassays or enzyme immunoassays.

The detection and determination of PP4 have diagnostic significance. PP4 is a tissue protein which occurs in relatively high concentrations only in certain organs. When these organs are diseased, as a result of increased cell destruction the concentration of the tissue protein $PP_4$ in serum or in other body fluids, for example in urine, of the patients can increase above the normal value. The detection and determination of $PP_4$ in body fluids can thus be employed to diagnose disease in these organs or can also be used as a marker for monitoring the progress of the illness and for checking therapy.

$PP_4$ can also be used to prepare antisera which can be employed to detect and determine $PP_4$.

The invention is illustrated by the examples which follows:

EXAMPLE 1

(A) Extraction of placentae and fractionation of the extract using an acridine base and ammonium sulfate 1,000 kg of deep-frozen human placentae were comminuted in a cutter-mixer and extracted with 1,000 liters of a 0.4% strength (g/100 ml) solution of sodium chloride. After removing the tissue residue by centrifugation, the extract was adjusted to pH 6.0 with 20% strength (g/100 ml) acetic acid and, with stirring, 200 liters of a 3% strength (g/100 ml) solution of 2-ethoxy-6,9-diaminoacridine lactate (Rivanol ®, Hoechst AG) were added. The precipitate was removed by centrifugation, 500 liters of a 2.5% strength (g/100 ml) solution of NaCl were added to it, and the mixture was stirred for 4 hours. The precipitated chloride of 2-ethoxy-6,9-diaminoacridine was removed by centrifugation. The companion proteins were partially precipitated from the supernatant by addition of 25% (g/100 ml) ammonium sulfate. Most of the protein $PP_4$ remained in solution; it was precipitated from this by addition of further ammonium sulfate (20 g/100 ml) and removed by centrifugation. This resulted in about 3 kg of a moist paste, which is called fraction A in the following text, being obtained.

(B) Gel filtration on Sephadex G-150

500 g of fraction A were dissolved in water, about 2.5 g of bentonite A (supplied by Erbsloh & Co., Geisenheim/Rh.) were added to remove the Rivanol which was still present, and, after centrifugation, the solution was dialyzed against a 0.01 mol/1 tris. HCl buffer (ph 8.0) which contained 0.05% (g/100 ml) $NaN_3$ (buffer solution I). The remaining solution was applied to a column (20×100 cm) filled with Sephadex G-150 and eluted with buffer solution I. The eluates containing the low molecular weight proteins (MW 10,000 to 60,000) were combined, and 45% (g/100 ml) ammonium sulfate was added to precipitate the proteins. The precipitate was removed by centrifugation (fraction B).

(C) Adsorption on kaolin and elution

Fraction B was dissolved in about 100 ml of water and dialyzed against buffer solution I. 15 g of kaolin (Bolus alba, supplied by Merck, Darmstadt) were added to each 150 ml of this solution, and the mixture was stirred at 20° C. for 1 hour. This resulted in $PP_4$ being bound to kaolin, while most of the other proteins remained in solution. After centrifugation, the kaolin was briefly washed twice with buffer solution I and then eluted twice consecutively with 150 ml of 0.1 mol/1 sodium phosphate buffer, ph 6.8, each time, this redissolving $PP_4$. After removing the kaolin by centrifugation, the eluates were combined and concentrated to 10–20 ml using an ultrafilter.

(D) Final purification

The product obtained by adsorption on kaolin had a purity of about 90%. It was possible to remove the major amount of the impurities still present by gel filtration on an Ultrogel AcA-44 column (4.5×100 cm) using a 0.1 mol/1 tris.HCl buffer solution of pH 8, which contained 1 mol/1 NaCl and 0.1% (g/100 ml) sodium azide (buffer solution II). The remaining serum proteins still present in traces were removed by inverse or negative immunoadsorption, ie. using carrier-bound antibodies from rabbits, which were directed against the proteins of human serum. The $PP_4$ isolated in this manner had a purity greater than 99%. The $PP_4$ solution was dialyzed against water and then freeze-dried. Yield about 30 mg of $PP_4$ from 500 g of paste of fraction A.

EXAMPLE 2

(A) Comminuting and washing the placentae

To isolate the membrane-associated fraction of $PP_4$, mature human placentae as are produced at delivery were comminuted in the frozen state using a slicer-mixer and stored in this form at −20° C. until used. First all soluble tissue proteins were removed by washing with physiological NaCl solution. For this purpose, 700 ml of NaCl solution were added to 500 g of the comminuted placental tissue, brief homogenization was carried out, then the mixture was stirred at 4° C. for several hours and finally centrifuged. The supernatant was discarded, and the residue was again stirred with 700 ml of NaCl solution for several hours, and again centrifuged. This washing procedure was repeated a total of 6 times. Soluble constituents were essentially removed from the placental tissue in this manner.

(B) Extraction of the placental tissue with detergent

To solubilize the membrane-associated antigens, the tissue residue after washing was extracted three times consecutively with 700 ml of a 2% strength solution of Triton ® X-100 in water each time, in each instance the mixture being stirred at 4° C. for 20 hours and then centrifuged. The extracts were first dialyzed against water and then against a 0.1 mol/1 tris.HCl buffer (pH 8.0) which contained 1 mol/1 NaCl and 0.1% (g 100 ml) sodium azide (buffer solution II). After dialysis, the solutions were each concentrated to about 200 ml using a ultrafilter (supplied by Amicon) with PM-10 membranes. The extracts from the residue from 500 g of placental tissue contained, on average, a total of about 25 mg of $PP_4$ (fraction 2A).

(C) Concentration of $PP_4$ by immunoadsorption (1) Preparation of the immunoadsorbent Polyvalent antisera were prepared by immunizing rabbits with the solubilized placental protein (Fraction 2A). They contained antibodies both to $PP_4$ and to other antigens made soluble with detergent. 350 ml of pooled antiserum of this type was dialyzed against 0.02 mol/1 phosphate buffer (pH 7.0) and chromatographed on DEAE-cellulose using the same buffer to separate the immunoglobulins. The immunoglobulin fraction which passed through (3.63 g of protein) was then reacted with 363 g of specially purified agarose in the form of beads (Sepharose ® from Pharmacia, Uppsala, Sweden) which had been activated with 45.3 g of cyanogen bromide, and was thus covalently bonded to this carrier. The process has been described by Axen et al., Nature 214 (1967) 1302. Using an immunoadsorbent prepared in this manner, it was possible further to concentrate PP$_4$, together with other solubilized antigens, from placental fraction 2A.

(2) Immunoadsorption procedure

The immunoadsorbent was suspended in buffer solution II, filled into a chromatography column (5.0×20 cm), and washed with buffer solution II. Then fraction 2A was applied to the column, and this resulted in PP$_4$ and other solubilized antigens being bound by immunoadsorption. The column was then thoroughly washed with buffer II. The adsorbed proteins were subsequently eluted from the column using about 600 ml of 6 mol/l urea solution. The elutates containing PP$_4$ were dialyzed against buffer solution II and concentrated to about 20 ml using an ultrafilter. Immediately after the elution of the proteins, the adsorbent in the column was again neutralized and thoroughly washed with buffer solution II. It was then employed for renewed binding of solubilized antigens by immunoadsorption.

(D) Removal of PP$_4$ by gel filtration

The separation of PP$_4$ from the other antigens bound by immunoadsorption was carried out by gel filtration on acrylamide/agarose AcA-34 (LKB, Stockholm). For this purpose, fractions obtained by immunoadsorption were combined, concentrated to 60 ml, and chromatographed on a AcA-34 column (5×110 cm) using buffer solution II. In this chromatography, PP$_4$ was clearly separated from the other solubilized membrane antigens, which mostly have a higher molecular weight (above 100,000) and thus migrate through the column faster than does PP$_4$. The fractions which contained the major amount of PP$_4$ were combined and concentrated to 10-20 ml using an ultrafilter.

(E) Final purification

The product obtained from gel filtration was still contaminated by small amounts of serum proteins, especially albumin. It was possible to remove these by inverse immunoadsorption, ie. using carrier-bound antibodies to the serum proteins still present as companion proteins.

I claim:

1. Protein PP$_4$, which has the following characteristics
   (a) an electrophoretic mobility in the range between that of $\alpha_1$ and $\alpha_2$ globulins;
   (b) an isoelectric point of 4.85±0.15;
   (c) a sedimentation coefficient $s_{20,w}^O$ of 3.3±0.2S;
   (d) a molecular weight determined in polyacrylamide gel containing sodium dodecylsulfate (DSD) of 35,000±5,000;
   (e) an extinction coefficient $E_1\ _{cm}^{1\%}$ (280 nm) of 5.9±0.6;
   (f) a carbohydrate content of 2.4±0.94% (g/100 g) (mannose 0.3±0.2%, galactose 0.4±0.2%, xylose 0.1±0.04%, glucose 0.2±0.1%, glucosamine 1.0±0.2% and neuraminic acid 0.4±0.2%) and
   (g) the following aminoacid composition:

| Aminoacid | Residues per 100 residues (mol-%) | Coefficient of variation |
|---|---|---|
| lysine | 6.95 | 1.14 |
| histidine | 0.97 | 17.4 |
| arginine | 5.44 | 1.77 |
| aspartic acid | 11.41 | 1.68 |
| threonine | 6.78 | 2.40 |
| serine | 6.21 | 2.26 |
| glutamic acid | 12.25 | 0.43 |
| proline | 1.96 | 6.20 |
| glycine | 6.68 | 3.83 |
| alanine | 7.92 | 1.67 |
| cystine ½ | 0.77 | 19.5 |
| valine | 5.34 | 3.80 |
| methionine | 1.98 | 6.00 |
| isoleucine | 5.21 | 2.23 |
| leucine | 11.50 | 0.45 |
| tyrosine | 3.55 | 4.21 |
| phenylalanine | 4.07 | 3.77 |
| tryptophan | 0.93 | 23.9 |

2. A process for isolating protein PP$_4$ which has
   (a) an electrophoretic mobility in the range between that of 60 1 and $\alpha_2$ globulins;
   (b) an isoelectric point of 4.85±0.15;
   (c) a sedimentation coefficient $s_{20,w}^O$ of 3.3±2S;
   (d) a molecular weight determined in polyacrylamide gel containing sodium dodecylsulfate (DSD) of 35,000±5,000;
   (e) an extinction coefficient $E_1\ _{cm}^{1\%}$ (280 nm) of 5.9±0.6;
   (f) a carbohydrate content of 2.4±0.94% (g/100 g) (mannose 0.3±0.2%, galactose 0.4±0.2%, xylose 0.1±0.04%, glucose 0.2±0.1%, glucosamine 1.0±0.2% and neuraminic acid 0.4±0.2%) and
   (g) the following aminoacid composition:

| Aminoacid | Residues per 100 residues (mol-%) | Coefficient of variation |
|---|---|---|
| lysine | 6.95 | 1.14 |
| histidine | 0.97 | 17.4 |
| arginine | 5.44 | 1.77 |
| aspartic acid | 11.41 | 1.68 |
| threonine | 6.78 | 2.40 |
| serine | 6.21 | 2.26 |
| glutamic acid | 12.25 | 0.43 |
| proline | 1.96 | 6.20 |
| glycine | 6.68 | 3.83 |
| alanine | 7.92 | 1.67 |
| cystine ½ | 0.77 | 19.5 |
| valine | 5.34 | 3.80 |
| methionine | 1.98 | 6.00 |
| isoleucine | 5.21 | 2.23 |
| leucine | 11.50 | 0.45 |
| tyrosine | 3.55 | 4.21 |
| phenylalanine | 4.07 | 3.77 |
| tryptophan | 0.93 | 23.9 | which comprises subjecting an extract isolated with dilute salt or buffer solutions from organs which contain this protein to one or more of the following measures:
   (a) precipitating the protein PP$_4$ with ammonium sulfate in the pH range from 5 to 8 and at 40-70% saturation;
   (b) precipitating the protein PP$_4$ with a water-soluble acridine base at a pH between 4 and 9 and at a concentration of the base of 0.2-0.8 g/100 ml;
   (c) preparative zone electrophoresis which entails the protein fraction between $\alpha_1$ and $\alpha_2$ globulins being isolated;

(d) gel filtration or ultrafiltration which entails proteins in the molecular weight range of 20,000 to 50,000 being isolated;
(e) adsorption on kaolin and elution of the protein $PP_4$;
(f) adsorption on a weakly basic ion exchanger and elution of the protein $PP_4$;
(g) concentration by immunoadsorption.

3. The process as claimed in claim 2, wherein organs which contain this protein are comminuted and washed with physiological saline until all soluble constituents have been removed, the tissue residue is then extracted with a solubilizing agent, preferably a solution of a non-ionic detergent, and the resulting extract is, after dialysis, treated as claimed in claim 2.

4. The use of the protein $PP_4$ for the preparation of antisera for detecting and determining $PP_4$ in body fluids, in order to diagnose diseases of particular organs, as a "marker" to monitor the progress of a disease or to check therapy.

* * * * *

UNITED STATES PATENT AND TRADEMARK OFFICE
CERTIFICATE OF CORRECTION

PATENT NO. : 4,507,229

DATED : March 26, 1985

INVENTOR(S) : Hans Bohn

It is certified that error appears in the above-identified patent and that said Letters Patent is hereby corrected as shown below:

In the Abstract, at Column 1, line 17, Claim 1 and Claim 2:

"$S_{20,w}{}^0$" should be -- $S^0_{20,w}$ --

In the Abstract, at Column 1, line 21, Claim 1 and Claim 2:

"$E_{1\ cm}{}^{1\%}$" should be -- $E^{1\%}_{1cm}$ --

In Claim 2, line 3, "$6\alpha_1$" should be -- $\alpha_1$ --.

Signed and Sealed this

Twenty-third Day of July 1985

[SEAL]

Attest:

DONALD J. QUIGG

Attesting Officer     Acting Commissioner of Patents and Trademarks